(12) United States Patent
Galli et al.

(10) Patent No.: US 7,476,674 B2
(45) Date of Patent: Jan. 13, 2009

(54) DERIVATIVES OF 5-PYRIDAZINYL-1-AZABICYCLO[3.2.1]OCTANE, PREPARATION METHOD THEREOF AND USE OF SAME IN THERAPEUTICS

(75) Inventors: Frederic Galli, Vaucresson (FR); Odile Leclerc, Massy (FR); Alistair Lochead, Charenton le Pont (FR); Julien Vache, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/029,008

(22) Filed: Feb. 11, 2008

(65) Prior Publication Data

US 2008/0176855 A1 Jul. 24, 2008

Related U.S. Application Data

(63) Continuation of application No. PCT/FR2006/001911, filed on Aug. 7, 2006.

(30) Foreign Application Priority Data

Aug. 18, 2005 (FR) .................................. 0508594

(51) Int. Cl.
*C07D 403/04* (2006.01)
*C07D 403/14* (2006.01)
*A61K 31/501* (2006.01)
(52) U.S. Cl. .................. 514/252.04; 544/238
(58) Field of Classification Search ............. 544/238; 514/252.04
See application file for complete search history.

(56) References Cited

FOREIGN PATENT DOCUMENTS

| WO | WO 00/34279 | 6/2000 |
| WO | WO 00/34284 | 6/2000 |
| WO | WO 03/057697 | 7/2003 |

OTHER PUBLICATIONS

Holladay, M. W., et. al., Neuronal Nicotinic Acetylchloline Receptors as Targets for Drug Discovery, Journal of Medicnal Chemistry, vol. 40, No. 26, (1997) pp. 4169-4194.

*Primary Examiner*—Kahsay T Habte
(74) *Attorney, Agent, or Firm*—Balaram Gupta

(57) ABSTRACT

The invention relates to compounds having general formula (I), wherein R is as defined herein.

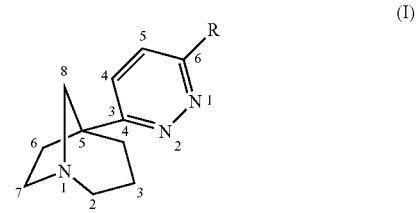

(I)

The invention also relates to acid addition salt, a hydrate or a solvate of compounds of formula (I). The invention further relates to the method of preparing said compounds and to the use of same in therapeutics.

16 Claims, No Drawings

DERIVATIVES OF 5-PYRIDAZINYL-1-AZABICYCLO[3.2.1]OCTANE, PREPARATION METHOD THEREOF AND USE OF SAME IN THERAPEUTICS

This application is a continuation of International application No. PCT/FR2006/001,911, filed Aug. 7, 2007, which is incorporated herein by reference in its entirety; which claims the benefit of priority of French Patent Application No. 05/08, 594, filed Aug. 18, 2005.

The present invention relates to 5-pyridazinyl-1-azabicyclo[3.2.1]octane derivatives, to the preparation thereof and to therapeutic use thereof.

A subject of the present invention is the compounds corresponding to formula (I)

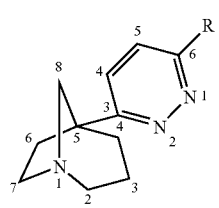

(I)

in which:

R is either a hydrogen or halogen atom;

or a phenyl group optionally substituted with one or more halogen atoms, or with one or more groups selected from $(C_1\text{-}C_6)$alkyl, $(C_1\text{-}C_6)$alkoxy, nitro, amino, di$(C_1\text{-}C_3)$alkylamino, trifluoromethyl, trifluoromethoxy, cyano, hydroxyl, acetyl or methylenedioxy groups;

or a group selected from a pyridinyl, pyrazolyl, imidazolyl, triazolyl, tetrazolyl, oxazolyl, thiazolyl, oxadiazolyl, thiadiazolyl, thienyl, furyl, isoxazolyl, isothiazolyl, pyrrolyl and naphthyl, it being possible for this group to be optionally substituted with one or more groups selected from halogen atoms, and $(C_1\text{-}C_6)$alkyl, $(C_1\text{-}C_6)$alkoxy, trifluoromethoxy, trifluoromethyl, nitro, cyano, hydroxyl, amino, $(C_1\text{-}C_6)$alkylamino or di$(C_1\text{-}C_6)$alkylamino groups.

Moreover, the carbon atom in the 5-position with respect to the azabicyclo[3.2.1]octane ring is asymmetrical, such that the compounds of the invention can exist in the form of two enantiomers or of a mixture of the latter. These enantiomers and also mixtures thereof, including racemic mixtures, are part of the invention.

The compounds of formula (I) can also exist in the form of bases or of addition salts with acids. Such addition salts are part of the invention.

The salts can be prepared with pharmaceutically acceptable acids, but the salts of other acids which are useful, for example for the purification or isolation of the compounds of formula (I), are also part of the invention.

The compounds of formula (I) can also exist in the form of hydrates or of solvates, i.e. in the form of associations or of combinations with one or more molecules of water or with a solvent. Such hydrates or solvates are also part of the invention.

In the context of the present invention:

the term "a halogen atom" is intended to mean: a fluorine, chlorine, bromine or iodine atom;

the term "an alkyl group" is intended to mean: a linear or branched, saturated aliphatic group. By way of examples, mention may be made of methyl, ethyl, propyl, isopropyl, butyl, isobutyl, tert-butyl, pentyl, etc, groups;

the term "an alkoxy group" is intended to mean: an —O—alkyl radical in which the alkyl group is as defined above.

Among the compounds of formula (I) which are subjects of the invention, a first subgroup of compounds comprises the compounds for which:

R is either a halogen atom, more particularly a chlorine;

or a phenyl group optionally substituted with one or more halogen atoms, more particularly chlorine or fluorine atoms, or with one or more groups selected from $(C_1\text{-}C_6)$alkyl groups, more particularly methyl, and $(C_1\text{-}C_6)$alkoxy groups, more particularly methoxy;

or a group selected from a pyridinyl, pyrazolyl, imidazolyl, triazolyl, tetrazolyl, oxazolyl, thiazolyl, oxadiazolyl, thiadiazolyl, thienyl, furyl, isoxazolyl, isothiazolyl, pyrrolyl and naphthyl, it being possible for this group to be optionally substituted with one or more $(C_1\text{-}C_6)$alkyl groups, more particularly methyl.

Among the compounds of formula (I) which are subjects of the invention, a second subgroup of compounds comprises the compounds for which:

R is either a halogen atom, more particularly a chlorine;

or a phenyl group optionally substituted with one or more halogen atoms, more particularly chlorine or fluorine atoms, or with one or more groups selected from $(C_1\text{-}C_6)$alkyl groups, more particularly methyl, and $(C_1\text{-}C_6)$alkoxy groups, more particularly methoxy;

or a group selected from a pyridinyl, pyrazolyl, imidazolyl, thienyl, furyl, and pyrrolyl, it being possible for this group to be optionally substituted with one or more $(C_1\text{-}C_6)$alkyl, more particularly methyl.

In the subsequent text, the term "protective group" is intended to mean a group which makes it possible, firstly, to protect a reactive function such as a hydroxyl or an amine during a synthesis and, secondly, to regenerate the intact reactive function at the end of synthesis. Examples of protective groups and also of the methods of protection and of deprotection are given in "Protective Groups in Organic Synthesis", Green et al., $2^{nd}$ Edition (John Wiley & Sons, Inc., New York), 1991.

In the subsequent text, the term "leaving group" is intended to mean a group which can be readily cleaved from a molecule by breaking of a heterolytic bond, with the departure of a pair of electrons. This group can thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and also of the references for preparing them are given in "Advances in Organic Chemistry", J. March, 3rd Edition, Wiley Interscience, 1985, p. 310-316.

In accordance with the invention, the compounds of formula (I) can be prepared by means of a process illustrated by scheme 1 which follows.

The compound of formula (II), in which PPh$_3$ denotes a triphenylphosphine group, is reacted with ethyl glyoxylate so as to obtain a compound of formula (III). The reduction of the ethylenic double bond gives a compound of formula (IV) which is reacted with a hydrazine hydrate so as to obtain a compound of formula (V). The latter is treated with bromine in acetic acid so as to obtain a compound of formula (VI).

Treatment of this compound with phosphorus oxychloride produces the compound of formula (VII). The compounds of formula (I) can subsequently be prepared from the compounds of formula (VII) according to any known methods, such as, for example:

- with a boronic acid of formula R—B(OH)$_2$ in which R is as defined in formula (I), in the presence of a palladium catalyst, for example tetrakistriphenylphosphine palladium;
- with a compound of formula R—H in which R is as defined in formula (I), in the presence of a strong base, for example sodium hydrate, in a solvent, for example dimethylformamide;
- with a stannous derivative of formula R—Sn[(CH$_2$)$_3$CH$_3$]$_3$ in which R is as defined in formula (I), in the presence of a palladium catalyst, for example bis(triphenylphosphino)dichloropalladium;
- with a compound of formula R—H in which R is as defined in formula (I), in the presence of n-butyllithium, of zinc chloride and of a palladium catalyst, for example tetrakistriphenylphosphine palladium.

The compound of formula (II) is accessible by means of methods described in the literature, such as, for example, in *J. Med. Chem.* 1992, 2392.

In scheme 1, the starting compounds and the reactants, when the method of preparing them is not described, are commercially available or are described in the literature, or else can be prepared according to methods which are described therein or which are known to those skilled in the art.

According to another of its aspects, a subject of the invention is also the compounds of formulae (II) to (VII). These compounds are useful as intermediates for synthesis of the compounds of formula (I).

The following examples describe the preparation of certain compounds in accordance with the invention. These examples are not limiting and mainly illustrate the present invention. The numbers of the compounds given between parentheses in the titles refer to those given in the first column of the table hereinafter, which illustrates the chemical structures and the physical properties of some compounds according to the invention.

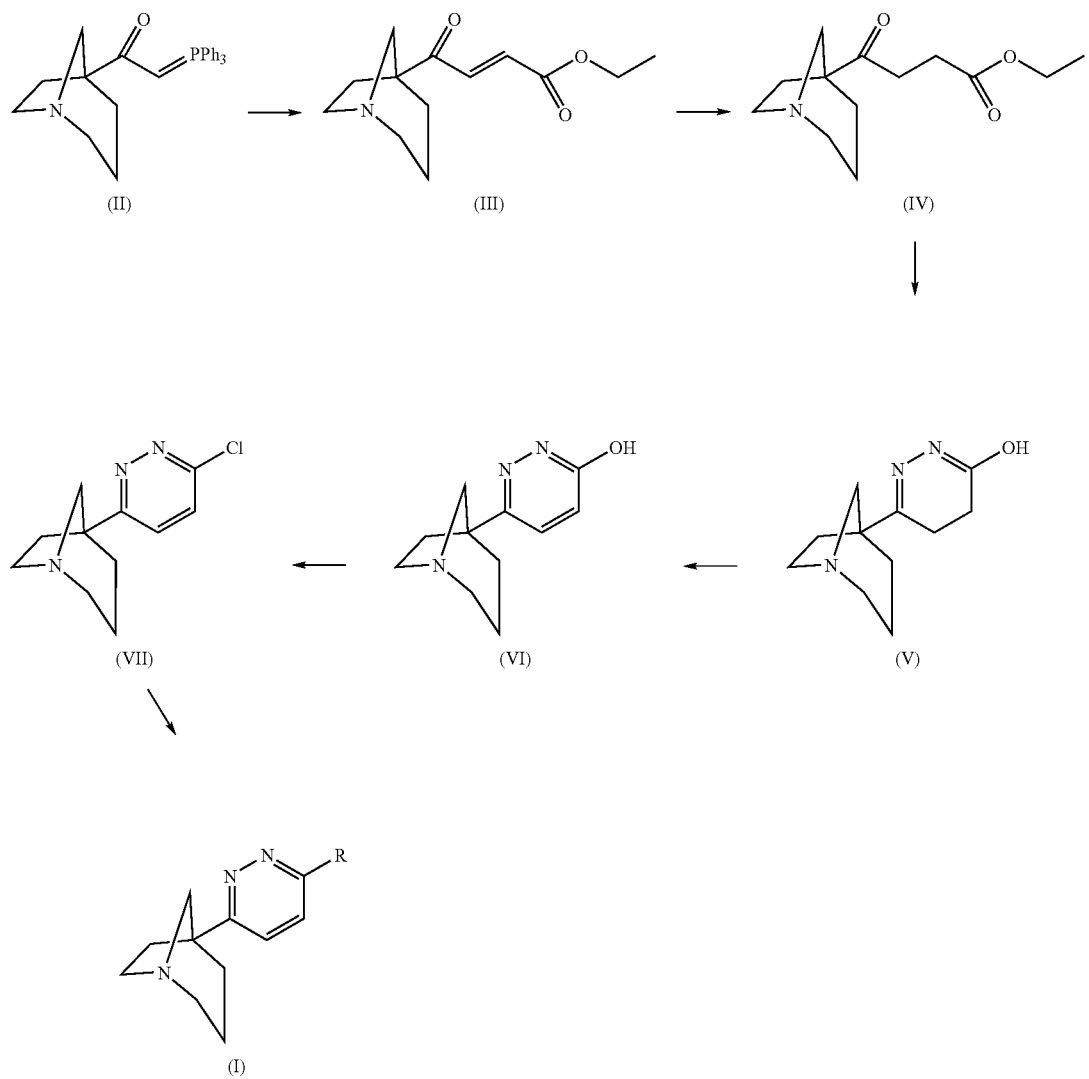

Scheme 1

EXAMPLE 1

Compound No. 1

5-(6-Phenylpyridazin-3-yl)-1-azabicyclo[3.2.1]octane

1.1. Ethyl (2E)-4-(1-azabicyclo[3.2.1]oct-5-yl)-4-oxobut-2-enoate 5.00 g (12.09 mmol) of 1-(1-azabicyclo[3.2.1]oct-5-yl)-2-(triphenylphosphanylidene)-ethanone in solution in 20 ml of chloroform and 20 ml of toluene are introduced into a 100 ml three-necked round-bottomed flask. 1.36 g (13.3 mmol) of ethyl glyoxylate are subsequently added and the reaction medium is refluxed at ambient temperature for 15 min. The solvent is eliminated by evaporation under reduced pressure and the residue obtained is purified by silica gel column chromatography, elution being carried out with a mixture of chloroform, methanol and aqueous ammonia in the proportions 89/2/0.2. 1.44 g of product are obtained in the form of an amorphous solid.

1.2. Ethyl 4-(1-azabicyclo[3.2.1]oct-5-yl)-4-oxobutanoate 2.95 g (12.43 mmol) of ethyl (2E)-4-(1-azabicyclo[3.2.1]oct-5-yl)-4-oxobut-2-enoate, as obtained in stage 1.1, in solution in 100 ml of ethyl alcohol are introduced into a hydrogenation flask in the presence of 0.4 g of palladium adsorbed under charcoal at 5%. The medium is stirred under approximately 0.28 MPa of hydrogen for 1 h at ambient temperature and is then filtered over diatomaceous earth, and the solvent is eliminated by evaporation under reduced pressure.

2.97 g of expected products are obtained in the form of an amorphous solid.

1.3. 6-(1-Azabicyclo[3.2.1]oct-5-yl)-4,5-dihydropyridazin-3-ol 2.90 g (12.12 mmol) of ethyl 4-(1-azabicyclo[3.2.1]oct-5-yl)-4-oxobutanoate, obtained in stage 1.2, in solution in 50 ml of ethyl alcohol are introduced into a 250 ml three-necked round-bottomed flask. 1.94 g (60.59 mmol) of hydrazine hydrate are subsequently added and the reaction medium is refluxed for 15 h. The solvent is evaporated to dryness under reduced pressure and the residue is purified by silica gel column chromatography, elution being carried out with a mixture of chloroform, methanol and aqueous ammonia in the proportions 90/10/1.

1.6 g of expected product are obtained in the form of an amorphous solid.

1.4. 6-(1-Azabicyclo[3.2.1]oct-5-yl)pyridazin-3-ol hydrobromide (1:1)

1.54 g (7.43 mmol) of 6-(1-azabicyclo[3.2.1]oct-5-yl)-4,5-dihydropyridazin-3-ol, obtained in stage 1.3, in solution in 20 ml of acetic acid are introduced into a 50 ml three-necked round-bottomed flask. The medium is heated to 70° C. and 1.31 g (8.17 mmol) of bromine are added. The mixture is stirred for 15 min and a further 1.31 g (8.17 mmol) of bromine are added. The reaction medium is subsequently heated at 100° C. for 2 h. The solvent is eliminated by filtration and the residue is triturated in methanol. The crystals obtained are collected by filtration under reduced pressure.

2 g of expected product are obtained.

Melting point: 196-198° C.

1.5. 5-(6-Chloropyridazin-3-yl)-1-azabicyclo[3.2.1]octane 2.1 g (7.34 mmol) of 6-(1-azabicyclo[3.2.1]oct-5-yl)pyridazin-3-ol hydrobromide (1:1), as obtained in stage 1.4, in solution in 15 ml of phosphorus oxychloride, are introduced into a 50 ml three-necked round-bottomed flask. The reaction medium is heated at 130° C. for 30 min and is then poured onto 500 ml of ice-cold water. The aqueous phase is then alkanized (i.e., basified) by adding a 30% aqueous sodium hydroxide solution and is extracted with chloroform. The combined organic phases are dried over magnesium sulfate, filtered, and concentrated under reduced pressure.

1.56 g of product are obtained in the form of a solid.

Melting point: 139-141° C.

1.6. (+) or (−)-5-(6-Chloropyridazin-3-yl)-1-azabicyclo[3.2.1]octane

The racemic mixture of 5-(6-chloropyridazin-3-yl)-1-azabicyclo[3.2.1]octane, obtained in stage 1.5, is dissolved by liquid chromatography on a chiral support so as to obtain the dextrorotary and levorotary enantiomers, respectively, (+)-5-(6-chloropyridazin-3-yl)-1-azabicyclo[3.2.1]octane and (−)-5-(6-chloropyridazin-3-yl)-1-azabicyclo[3.2.1]octane.

(+)-5-(6-Chloropyridazin-3-yl)-1-azabicyclo[3.2.1]octane: $[\alpha_D^{20}]=+30.9°$ (c=1, $CH_3OH$)

(−)-5-(6-Chloropyridazin-3-yl)-1-azabicyclo[3.2.1]octane: $[\alpha_D^{20}]=-17°$ (c=1, $CH_3OH$)

1.7. 5-(6-Phenylpyridazin-3-yl)-1-azabicyclo[3.2.1]octane 0.3 g (1.34 mmol) of 5-(6-chloropyridazin-3-yl)-1-azabicyclo[3.2.1]octane, obtained in stage 1.5, and 0.245 g (2.01 mmol) of phenylboronic acid in solution in 8 ml of toluene are introduced successively into a 25 ml three-necked round-bottomed flask. 1.42 ml (2.84 mmol) of a 2M aqueous sodium carbonate solution, 1.5 ml of ethanol and 0.0465 g (0.04 mmol) of tetrakis(triphenylphosphino)palladium are subsequently added. The mixture is refluxed for 20 h, cooled to ambient temperature, and poured onto 20 ml of water. The aqueous phase is extracted three times with 30 ml of chloroform, and the combined organic phases are dried over magnesium sulfate and concentrated under reduced pressure. The residue is purified by silica gel column chromatography, elution being carried out with a mixture of chloroform, methanol and aqueous ammonia in the proportions 95/5/0.5.

0.32 g of expected product is as obtained in the form of crystals.

Melting point: 133-134° C.

$^1$H NMR ($CDCl_3$) δ (ppm): 8.15 (2H, d); 7.85 (1H, d); 7.60-7.40 (4H, m); 3.40-2.80 (6H, m); 2.30 (2H, t); 2.15-1.85 (2H, m); 1.80 (1H, s); 1.70-1.50 (1H, m).

Compounds Nos. 2, 3 and 14 were prepared according to the method described in Example 1.

EXAMPLE 2

Compound No. 5

5-[6-(5-Methyl-2-thienyl)pyridazin-3-yl]-1-azabicyclo[3.2.1]octane hydrochloride (1:1)

This compound is obtained according to the method described in stage 1.6 of Example 1, using 5-(6-chloropyridazin-3-yl)-1-azabicyclo[3.2.1]octane, prepared according to stage 1.5 of Example 1, and 5-methylsulfanyl-2-thienylboronic acid. The hydrochloride thereof is prepared by treatment of the base with a solution of hydrochloric acid in propan-2-ol, and the crystals obtained are collected by filtration and dried under vacuum.

Melting point: 245-246° C.

$^1$H NMR (DMSO) δ (ppm): 8.15 (1H, d); 7.75 (1H, d); 7.75 (1H, d); 6.95 (1H, d); 3.75-3.25 (6H, m); 2.45 (3H, s); 2.15-1.85 (6H, m).

Compounds Nos. 6 to 11 were prepared according to the method described in Example 2.

Compounds Nos. 12, 13, 16, 17, 22 and 23 were prepared according to the method described in Example 2, using (+)-5-(6-chloropyridazin-3-yl)-1-azabicyclo[3.2.1]octane, obtained by resolution of the racemic mixture (prepared in stage 1.5 of Example 1) by liquid chromatography on a chiral support.

Compounds Nos. 15, 20 and 21 were prepared according to the method described in Example 2, using (−)-5-(6-chloropyridazin-3-yl)-1-azabicyclo[3.2.1]octane, obtained by resolution of the racemic mixture (prepared in stage 1.5 of Example 1) by liquid chromatography on a chiral support.

EXAMPLE 3

Compound No. 25

(+)-5-[6-(−1H-1 imidazol-1-yl)pyridazin-3-yl]-1-azabicyclo[3.2.1]octane 0.228 g (3.35 mmol) of imidazole in solution in 4 ml of dimethylformamide is introduced into a 10 ml three-necked round-bottomed flask. 0.137 g (3.42 mmol) of sodium hydride as a 60% dispersion in oil is subsequently added and the mixture is stirred at ambient temperature for 1 hour. The mixture is then added to a solution of (+)-5-(6-chloropyridazin-3-yl)-1-azabicyclo[3.2.1]octane (obtained by resolution of the racemic mixture prepared in stage 1.5 of Example 1, by liquid chromatography on a chiral support) (0.15 g, 0.67 mmol) in dimethylformamide and the reaction medium is heated at 90° C. for 15 hours and then at 110° C. for 3 hours, and the solvent is evaporated off under reduced pressure. The residue is taken up in 10 ml of chloroform and 10 ml of a saturated aqueous sodium carbonate solution. The aqueous phase is extracted again with 10 ml of chloroform and the combined organic phases are washed with a saturated aqueous sodium chloride solution, dried over sodium sulfate, filtered, and concentrated under reduced pressure. The residue is purified by silica gel plate chromatography, elution being carried out with a mixture of chloroform, methanol and aqueous ammonia in the proportions 85/15/1.5. 0.111 g of expected product is obtained.

Melting point: 177-179° C.

$^1$H NMR (DMSO) δ (ppm): 8.55 (1H, s); 8.10 (1H, d); 8.00 (1H, s); 7.85 (1H, d); 7.15 (1H, s); 3.15-2.70 (6H, m); 2.25-1.75 (5H, m); 1.60-1.35 (1H, t).

Compound No. 26 was prepared according to the method described in Example 3.

EXAMPLE 4

Compound No. 19

(+)-5-[6-(−1H-Imidazol-4-yl)pyridazin-3-yl]-1-azabicyclo[3.2.1]octane hydrochloride (2:1)

4.1. (+)-5-[6-(1-Triphenylmethylimidazol-4-yl)pyridazin-3-yl]-1-azabicyclo[3.2.1]octane 0.14 g (0.63 mmol) of (+)-5-(6-chloropyridazin-3-yl)-1-azabicyclo[3.2.1]octane (obtained by resolution of the racemic mixture prepared in stage 1.5 of Example 1 by liquid chromatography on a chiral support) (0.15 g, 0.67 mmol) in solution in 3 ml of tetrahydrofuran, 0.94 g (1.56 mmol) of 1-triphenylmethyl-4-tributylstannylimidazole and 0.027 g (0.037 mmol) of bis(triphenylphosphino)dichloropalladium are introduced successively into a 10 ml three-necked round-bottomed flask. The mixture is then heated at 100° C. under an argon atmosphere for 15 hours and then diluted in 10 ml of chloroform and 10 ml of a saturated aqueous sodium carbonate solution. The aqueous phase is extracted again with 10 ml of chloroform and the combined organic phases are washed with a saturated aqueous sodium chloride solution, dried over sodium sulfate, filtered, and concentrated under reduced pressure. The residue is purified by silica gel column chromatography, elution being carried out with a mixture of chloroform, methanol and aqueous ammonia in the proportions 96/4/0.4. The expected product, contaminated with excess 1-triphenylmethyl-4-tributylstannylimidazole, is obtained in the form of an amorphous solid.

4.2. (+)-5-[6-(−1H-Imidazol-4-yl)pyridazin-3-yl]-1-azabicyclo[3.2.1]octane hydrochloride (2:1)

The residue of (+)-5-[6-(−1-triphenylmethylimidazol-4-yl)pyridazin-3-yl]-1-azabicyclo-[3.2.1]octane, obtained in stage 4.1, in solution in 4 ml of methanol, is introduced into a 10 ml three-necked round-bottomed flask. 0.6 ml of a 6N solution of hydrochloric acid in isopropyl alcohol is subsequently added and the reaction medium is heated at 80° C. for 3 hours. The solvent is concentrated under reduced pressure and the residue is triturated in diethyl ether. The crystals obtained are collected by filtration and dried under vacuum.

0.12 g of product is obtained.

Melting point: 269-271° C.

$^1$H NMR (DMSO) δ (ppm): 11.20 (1H, s); 9.10 (1H, s); 8.45 (1H, s); 8.35 (1H, d); 7.95 (1H, d); 3.70 (2H, s); 3.60-3.45 (2H, t); 3.30 (2H, d); 2.45-1.85 (6H, m).

Compound No. 18 was prepared according to the method described in Example 4, using (−)-5-(6-chloropyridazin-3-yl)-1-azabicyclo[3.2.1]octane, obtained by resolution of the racemic mixture (prepared in stage 1.5 of Example 1) by liquid chromatography on a chiral support.

EXAMPLE 5

Compound No. 24

(−)-5-[6-(−1H-Imidazol-2-yl)pyridazin-3-yl]-1-azabicyclo[3.2.1]octane hydrobromide (2:1)

0.39 g (2.23 mmol) of 1-(dimethylaminosulfonyl)imidazole in solution in 10 ml of tetrahydrofuran is introduced into a 25 ml three-necked flask. The reaction medium is cooled to −78° C. and 1.4 ml of a 1.6M solution of n-butyllithium in hexane are added, dropwise, in 20 minutes. 0.31 g (2.32 mmol) of zinc chloride in solution in 4 ml of tetrahydrofuran is subsequently added. The mixture is stirred while allowing the temperature to come back up to 20° C., and then 0.48 g (3.58 mmol) of zinc chloride, 0.06 g (0.05 mmol) of tetrakis (triphenylphosphino)palladium and 0.2 g (0.89 mmol) of (−)-5-(6-chloropyridazin-3-yl)-1-azabicyclo[3.2.1]octane (obtained by resolution of the racemic mixture prepared in stage 1.5 of Example 1, by liquid chromatography on a chiral support) in solution in 5 ml of tetrahydrofuran are successively added. The mixture is then refluxed for 24 hours and then cooled to ambient temperature. 30 ml of a 30% aqueous sodium hydroxide solution and 50 ml of chloroform are added. The aqueous phase is extracted with chloroform and the combined organic phases are then washed with a saturated aqueous sodium chloride solution, dried over sodium sulfate, filtered, and concentrated under reduced pressure.

The residue obtained is solubilized in 10 ml of dioxane and 1.5 ml of a 2N aqueous hydrochloric acid solution. The medium is stirred at ambient temperature for 2 hours and the solvent is then evaporated off under reduced pressure. The residue is taken up in 30 ml of chloroform and 30 ml of a saturated aqueous sodium carbonate solution. The aqueous phase is extracted with chloroform and the combined organic phases are dried over sodium sulfate, filtered, and concentrated under reduced pressure. The residue is purified by silica gel column chromatography, elution being carried out with a mixture of chloroform, methanol and aqueous ammonia in the proportions 90/10/1. 0.033 g of expected product is obtained, which product is dissolved in 3 ml of isopropyl alcohol in order to add 0.045 ml of a 5.7N solution of hydrobromic acid in acetic acid. The crystals formed are collected by filtration and dried under vacuum. 0.027 g of product is obtained.

Melting point: 290-292° C.

$^1$H NMR (DMSO) δ (ppm): 10.15 (1H, s); 8.40 (1H, d); 8.05 (1H, d); 7.80 (2H, s); 3.80 (1H, s); 3.70-3.50 (2H, t); 3.35 (2H, d); 2.45-1.85 (6H, m).

Table 1 which follows illustrates the chemical structures and the physical properties of some examples of compounds according to the invention. In this table:

in the column [$\alpha_D^{20}$] (CH$_3$OH), the value indicated is the optical rotation of the compound, the concentration in g/100 ml in methanol at which this measurement was carried out being indicated between parentheses; the compounds with no indication in this column are racemates;

in the column "Salt", "−" denotes a compound in the form of a base, "HBr" denotes a hydrobromide and "HCl" denotes a hydrochloride. The acid:base molar ratios are indicated opposite.

TABLE 1

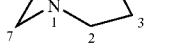

(I)

| No. | R | Salt | [$\alpha_D^{20}$] (CH$_3$OH) | PF (° C.) (Melting point) |
|---|---|---|---|---|
| 1 | C$_6$H$_5$ | — | — | 133-134 |
| 2 | 3-furyl | — | — | 140-141 |
| 3 | 4-CH$_3$-2-thienyl | — | — | 139-140 |
| 4 | Cl | HCl 1:1 | — | 234-235 |
| 5 | 5-CH$_3$-2-thienyl | HCl 1:1 | — | 245-246 |
| 6 | 3,5-(CH$_3$)$_2$—C$_6$H$_3$ | HCl 1:1 | — | 182-184 |
| 7 | 4-OCH$_3$—C$_6$H$_4$ | HCl 1:1 | — | 229-231 |
| 8 | 2-furyl | HCl 1:1 | — | 274-275 |
| 9 | 3,4-(OCH$_3$)$_2$—C$_6$H$_3$ | HCl 1:1 | — | 224-226 |
| 10 | 3-F—C$_6$H$_4$ | HCl 1:1 | — | 269-270 |
| 11 | 3-Cl—C$_6$H$_4$ | HCl 1:1 | — | 231-232 |
| 12 | 3,5-(CH$_3$)$_2$-4-pyrazolyl | HCl 1:1 | n.d.* enantiomer (+) | 260-261 |
| 13 | 2-pyrrolyl | — | +39.6 (c = 0.6) | 207-209 |
| 14 | 3-pyridinyl | — | — | 131-133 |
| 15 | 5-CH$_3$-2-thienyl | HCl 1:1 | −17 (c = 0.45) | 270-272 |
| 16 | 3-furyl | HCl 1:1 | +14.1 (c = 0.3) | 226-228 |
| 17 | 5-CH$_3$-2-thienyl | HCl 1:1 | +20.6 (c = 0.38) | 269-271 |
| 18 | 4-imidazolyl | HCl 2:1 | −18.2 (c = 1) | 271-273 |
| 19 | 4-imidazolyl | HCl 2:1 | +15.8 (c = 1) | 269-271 |
| 20 | 4-pyrazolyl | HBr 2:1 | −17.1 (c = 1) | 221-223 |
| 21 | 1-CH$_3$-4-pyrazolyl | HBr 2:1 | −17 (c = 1) | 273-275 |
| 22 | 4-pyrazolyl | HBr 2:1 | +14.9 (c = 0.7) | 295-297 |
| 23 | 1-CH$_3$-4-pyrazolyl | HBr 2:1 | +15.4 (c = 1) | 279-281 |
| 24 | 2-imidazolyl | HBr 2:1 | −15.3 (c = 0.65) | 290-292 |
| 25 | 1-imidazolyl | — | +63.6 (c = 0.2**) | 177-179 |
| 26 | 1-imidazolyl | — | −49.5 (c = 0.4) | 177-179 |

*n.d. = value not determined
**concentration in g/100 ml in DMSO

The compounds of the invention were subjected to pharmacological assays which demonstrated their advantage as active substances of medicaments.

Thus, they were studied with regard to their affinity with respect to nicotinic receptors containing the $\alpha_7$ subunit, according to the methods described by Mark and Collins in *J. Pharmacol. Exp. Ther.* 1982, 22, 564 and by Marks et al. in *Mol. Pharmacol.* 1986, 30, 427.

Male OFA rats weighing 150 to 200 g are decapitated, and the entire brain is rapidly removed, homogenized using a Polytron™ grinder in 15 volumes of a 0.32 M sucrose solution at 4° C., and then centrifuged at 1000 G for 10 min. The pellet is removed and the supernatant is centrifuged at 8000 G for 20 min at 4° C. The pellet is recovered, homogenized using a Polytron™ grinder in 15 volumes of double-distilled water at 4° C., and then centrifuged at 8000 G for 20 min. The pellet is removed and supernatant and the buffy coat are centrifuged at 40 000 G for 20 min. The pellet is recovered, and is suspended in 15 volumes of double-distilled water at 4° C. and centrifuged once again at 40 000 G for 20 min before being stored at −80° C.

On the day of the experiment, the tissue is slowly thawed and is suspended in 5 volumes of buffer. 150 μl of this membrane suspension are preincubated at 37° C. for 30 min, in the dark, in the presence or absence of the test compound. The membranes are then incubated for 60 min at 37° C., in the dark, in the presence of 50 μL of 1 nM [$^3$H]-α-bungarotoxin in a final volume of 250 μL of 20 mM HEPES buffer containing 0.05% polyethyleneimine. The reaction is stopped by filtration over GF/C™ Whatman filters pretreated for 3 h with 0.05% polyethyleneimine. The filters are rinsed with twice 5 ml of buffer at 4° C. and the radioactivity retained on each filter is measured by liquid scintigraphy. The non-specific binding is determined in the presence of α-bungarotoxin at a final concentration of 1 μM; the non-specific binding represents approximately 60% of the total binding recovered on the filter. For each concentration of compound studied, the percentage inhibition of the specific binding of [$^3$H]-α-bungarotoxin is determined, and then the $IC_{50}$, concentration of compound which inhibits 50% of the specific binding, is calculated.

The $IC_{50}$ values of the compounds of the invention with most affinity lie between 0.001 and 1 μM.

The compounds of the invention were also studied with regard to their affinity with respect to nicotinic receptors containing the $\alpha_4\beta_2$ subunit according to the methods described by Anderson and Arneric in *Eur. J. Pharmacol.* 1994, 253, 261 and by Hall et al., in *Brain Res.* 1993, 600, 127.

Male Sprague Dawley rats weighing from 150 to 200 g are decapitated and the entire brain is rapidly removed, homogenized in 15 volumes of a 0.32 M sucrose solution at 4° C., and then centrifuged at 1000 G for 10 min. The pellet is removed and the supernatant is centrifuged at 20 000 G for 20 min at 4° C. The pellet is recovered and homogenized using a Polytron™ grinder in 15 volumes of double-distilled water at 4° C., and then centrifuged at 8000 G for 20 min. The pellet is removed and the supernatant and the buffy coat are centrifuged at 40 000 G for 20 min, and the pellet is recovered, resuspended in 15 ml of double-distilled water and centrifuged once again at 40 000 G before being stored at −80° C.

On the day of the experiment, the tissue is slowly thawed and is suspended in 3 volumes of buffer. 150 μl of this membrane suspension are incubated at 4° C. for 120 min in the presence of 100 μl of [$^3$H]-cytisine at 1 nM in a final volume of 500 μl of buffer, in the presence or absence of test compounds. The reaction is stopped by filtration on Whatman GF/B™ filters pretreated with polyethyleneimine, the filters are washed with twice 5 ml of buffer at 4° C., and the radioactivity retained on the filter is measured by liquid scintigraphy. The non-specific binding is determined in the presence of (−)-nicotine at 10 μM; the non-specific binding represents 75 to 85% of the total binding recovered on the filter. For each concentration of compounds studied, the percentage inhibition of the specific binding of [$^3$H]-cytisine, at doses of 1 μM and 10 μM, is determined. For the compounds of the invention with most affinity, the $IC_{50}$, concentration of compound which inhibits 50% of the specific binding, is calculated.

The $IC_{50}$ values of the compounds of the invention with most affinity lie between 0.2 and 10 μM.

The experimental data of some specific compounds are indicated in Table 2 below.

TABLE 2

| Compound No. | $IC_{50}\,\alpha_7$ (μM) | Percentage inhibition of the specific binding of [$^3$H]-cytisine at the dose of 1 μM, for the $\alpha_4\beta_2$ subunit (%) |
|---|---|---|
| 3 | 0.428 | 10 |
| 7 | 0.164 | 9 |
| 8 | 0.442 | 4 |

The compounds of the invention were also studied with regard to the affinity with respect to ganglionic peripheral nicotinic receptors according to the method described by Houghtling et al., in *Mol. Pharmacol.* 1995, 48, 280.

Bovine adrenal glands stored at −80° C. are poured and are homogenized using a Polytron™ grinder in 20 volumes of 50 mM Tris-HCl buffer, at pH 7.4, and at 4° C., and are then centrifuged at 35 000 G for 10 min. The supernatant is removed and the pellet is resuspended in 30 volumes of 50 mM Tris-HCl buffer, at 4° C., and the suspension is rehomogenized before being recentrifuged at 35 000 G for 10 min. The final pellet is taken up in 10 volumes of Tris-HCl buffer at 4° C. 100 μl of membranes, i.e. 10 mg of fresh tissue, are incubated at 24° C. for 3 h in the presence of 50 μl of [$^3$H]-epibatidine at a final concentration of 0.66 nM in a final volume of 250 μl of buffer, in the presence or absence of test compounds. The reaction is stopped by dilution of the samples with 50 μM Tris-HCl buffer, pH 7.4, at 4° C., and the filtration is carried out on Whatman GF/C™ filters pretreated for 3 hours with 0.5% polyethyleneimine. The filters are rinsed twice with 5 ml of buffer, and the radioactivity retained on the filter is measured by liquid scintigraphy. The non-specific binding is determined in the presence of (−)-nicotine at a final concentration of 2 mM; the non-specific binder represents 30 to 40% of the total binding recovered on the filter. For each concentration of product studied, the percentage inhibition of the specific binding of [$^3$H]-epibatidine is determined, and the $IC_{50}$, concentration of compound which inhibits 50% of the specific binding, is then calculated. The $IC_{50}$ values of the compounds of the invention lie between 1 and 10 μM.

The results obtained show that certain compounds of the invention are selective ligands for the $\alpha_7$ subunit of the nicotinic receptor and that others are mixed $\alpha_4\beta_2$ and $\alpha_7$.

These results suggest the use of the compounds in the treatment or prevention of disorders related to a nicotinic receptor dysfunction, in particular in the central nervous system.

These disorders including cognitive impairments, more specifically memory impairments (acquisition, consolidation and recall), but also affected attention processes, and problems with executive functions related to Alzheimer's disease, to pathological ageing (Age Associated Memory Impairment, AAMI) or normal ageing (senile dementia), to Parkinsonian syndrome, to trisomy 21 (Down's syndrome), to psychiatric pathologies (in particular cognitive problems associated with schizophrenia), to alcoholic Korsakoff's syndrome, to vascular dementias (multiinfarct dementia, MDI), to cranial traumas.

The compounds of the invention could also be used in the treatment of the motor problems observed in Parkinson's disease or other neurological diseases such as Huntington's chorea, Tourette's syndrome, late dyskinesia and hyperkinesia.

They may also exhibit a neuroprotective therapeutic activity with respect to anatomical-histopathological damage related to the abovementioned neurodegenerative diseases.

The compounds of the invention can also constitute a curative or symptomatic treatment of cerebral strokes and of hypoxic episodes in the brain. They can be used in the case of psychiatric pathologies: schizophrenia (positive and/or negative symptoms), bipolar disorders, depression, anxiety, panic attacks, attention deficit hyperactivity disorders, obsessive compulsive behaviors.

They can prevent the symptoms due to tobacco withdrawal, alcohol withdrawal, or withdrawal from the various substances which induce dependency, such as cocaine, LSD, cannabis or benzodiazepines.

They can be useful in the treatment of pain of various origins (including chronic, neuropathic or inflammatory pain).

Moreover, the compounds of the invention can be used for the treatment of lower limb ischemia, of obliterative arteritis of the lower limbs (PAD: peripheral arterial disease), of cardiac ischemia (stable angina), of myocardial infarction, of heart failure, of cutaneous cicatrisation deficiency in diabetic patients, and of varicose ulcers in venous insufficiency.

The compounds of the invention can also be used for the treatment of inflammatory processes of various origins, in particular inflammations concerning the central nervous system.

The compounds according to the invention can therefore be used for the preparation of medicaments, in particular of medicaments useful in the treatment or prevention of disorders related to a nicotinic receptor dysfunction, in particular of the disorders mentioned above.

Thus, according to another of its aspects, a subject of the invention is medicaments which comprise a compound of formula (I), or an addition salt of the latter with a pharmaceutically acceptable acid, or else a hydrate or a solvate of the compound of formula (I).

These medicaments find their use in therapeutics, in particular in the treatment or prevention of disorders related to a nicotinic receptor dysfunction, in particular of the disorders mentioned above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or solvate of said compound, and also at least one pharmaceutically acceptable excipient. Said excipients are selected according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its possible salt, solvate or hydrate, can be administered in unit administration form, as a mixture with conventional pharmaceutical excipients, to animals and to human beings for the prophylaxis or treatment of the above disorders or diseases.

The suitable unit administration forms comprise oral administration forms, such as tablets, soft or hard gelatine capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention are used in creams, gels, ointment or lotions.

By way of example, a unit administration form of a compound according to the invention in the form of a tablet can comprise the following components:

| Compounds according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

Said unit forms contain a dose so as to allow a daily administration of 0.01 to 20 mg of active ingredient per kg of body weight, according to the pharmaceutical form.

There may be specific cases where higher or lower dosages are appropriate: such dosages do not depart from the scope of the invention. According to the usual practice, the dosage appropriate for each patient is determined by the physician according to the method of administration, and the weight and response of said patient.

According to another of its aspects, the present invention also relates to a method of treatment of the pathologies indicated above, which comprises the administration, to a patient, of an effective dose of the compound according to the invention, or one of its pharmaceutically acceptable salts or hydrates or solvates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I):

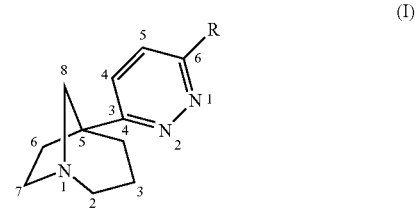

in which:
R is
either a hydrogen or halogen atom;
or a phenyl group optionally substituted with one or more halogen atoms, or with one or more groups selected from ($C_1$-$C_6$)alkyl, ($C_1$-$C_6$)alkoxy, nitro, amino, di($C_1$-$C_3$) alkylamino, trifluoromethyl, trifluoromethoxy, cyano, hydroxyl, acetyl or methylenedioxy groups;

or a group selected from pyridinyl, pyrazolyl, imidazolyl, triazolyl, tetrazolyl, oxazolyl, thiazolyl, oxadiazolyl, thiadiazolyl, thienyl, furyl, isoxazolyl, isothiazolyl, pyrrolyl and naphthyl, it being possible for this group to be optionally substituted with one or more groups selected from halogen atoms, and ($C_1$-$C_6$)alkyl, ($C_1$-$C_6$)alkoxy, trifluoromethoxy, trifluoromethyl, nitro, cyano, hydroxyl, amino, ($C_1$-$C_6$)alkylamino or di($C_1$-$C_6$)alkylamino groups;

or an acid addition salt thereof.

2. The compound of formula (I) according to claim 1, wherein

R is either a halogen atom, or a phenyl group optionally substituted with one or more halogen atoms, or with one or more groups selected from ($C_1$-$C_6$)alkyl and ($C_1$-$C_6$)alkoxy groups;

or a group selected from pyridinyl, pyrazolyl, imidazolyl, triazolyl, tetrazolyl, oxazolyl, thiazolyl, oxadiazolyl, thiadiazolyl, thienyl, furyl, isoxazolyl, isothiazolyl, pyrrolyl and naphthyl, it being possible for this group to be optionally substituted with one or more ($C_1$-$C_6$)alkyl groups, or an acid addition salt thereof.

3. The compound of formula (I) according to claim 1, wherein

R is either a halogen atom;

or a phenyl group optionally substituted with one or more halogen atoms, or with one or more groups selected from ($C_1$-$C_6$)alkyl and ($C_1$-$C_6$)alkoxy groups;

or a group selected from pyridinyl, pyrazolyl, imidazolyl, thienyl, furyl and pyrrolyl, it being possible for this group to be optionally substituted with one or more ($C_1$-$C_6$)alkyl groups;

or an acid addition salt thereof.

4. A process for preparing a compound of formula (I) according to claim 1 comprising:

reacting a compound of formula (VII):

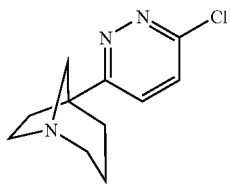

(VII)

either with a boronic acid of formula R—B(OH)$_2$ in which R is as defined in claim 1, in the presence of a palladium catalyst;

or with a compound of formula R—H in which R is as defined in claim 1, in the presence of a strong base in a solvent;

or with a stannous derivative of formula R—Sn[(CH$_2$)$_3$ CH$_3$]$_3$ in which R is as defined in claim 1, in the presence of a palladium catalyst;

or with a compound of formula R—H in which R is as defined in claim 1, in the presence of n-butyllithium, or zinc chloride or a palladium catalyst.

5. A pharmaceutical composition comprising a compound of formula (I) according to claim 1 or a pharmaceutically acceptable salt, a hydrate or a solvate thereof in combination with at least one pharmaceutically acceptable excipient.

6. A pharmaceutical composition comprising a compound of formula (I) according to claim 2 or a pharmaceutically acceptable salt, a hydrate or a solvate thereof in combination with at least one pharmaceutically acceptable excipient.

7. A pharmaceutical composition comprising a compound of formula (I) according to claim 3 or a pharmaceutically acceptable salt, a hydrate or a solvate thereof in combination with at least one pharmaceutically acceptable excipient.

8. A method of treating cerebral stroke, hypoxic episodes in the brain, or psychiatric pathologies comprising administering to a patient in need of said treatment a therapeutically effective amount of a compound of formula (I) according to claim 1 or a pharmaceutically acceptable salt thereof.

9. A method of treating cerebral stroke, hypoxic episodes in the brain, or psychiatric pathologies comprising administering to a patient in need of said treatment a therapeutically effective amount of a compound of formula (I) according to claim 2 or a pharmaceutically acceptable salt thereof.

10. A method of treating cerebral stroke, hypoxic episodes in the brain, or psychiatric pathologies comprising administering to a patient in need of said treatment a therapeutically effective amount of a compound of formula (I) according to claim 3 or a pharmaceutically acceptable salt thereof.

11. A method of treating pain comprising administering to a patient in need of said treatment a therapeutically effective amount of a compound of formula (I) according to claim 1 or a pharmaceutically acceptable salt or a hydrate or a solvate thereof.

12. A method of treating pain comprising administering to a patient in need of said treatment a therapeutically effective amount of a compound of formula (I) according to claim 2 or a pharmaceutically acceptable salt or a hydrate or a solvate thereof.

13. A method of treating pain comprising administering to a patient in need of said treatment a therapeutically effective amount of a compound of formula (I) according to claim 3 or a pharmaceutically acceptable salt or a hydrate or a solvate thereof.

14. A method of treating lower limb ischemia, obliterative arteritis of the lower limbs, cardiac ischemia, myocardial infarction, heart failure, cutaneous cicatrisation deficiency in diabetic patients, or varicose ulcers in venous insufficiency comprising administering to a patient in need of said treatment a therapeutically effective amount of a compound of formula (I) according to claim 1 or a pharmaceutically acceptable salt or a hydrate or a solvate thereof.

15. A method of treating lower limb ischemia, obliterative arteritis of the lower limbs, cardiac ischemia, myocardial infarction, heart failure, cutaneous cicatrisation deficiency in diabetic patients, or varicose ulcers in venous insufficiency comprising administering to a patient in need of said treatment a therapeutically effective amount of a compound of formula (I) according to claim 2 or a pharmaceutically acceptable salt or a hydrate or a solvate thereof.

16. A method of treating lower limb ischemia, obliterative arteritis of the lower limbs, cardiac ischemia, myocardial infarction, heart failure, cutaneous cicatrisation deficiency in diabetic patients, or varicose ulcers in venous insufficiency comprising administering to a patient in need of said treatment a therapeutically effective amount of a compound of formula (I) according to claim 3 or a pharmaceutically acceptable salt or a hydrate or a solvate thereof.

* * * * *